(12) United States Patent
Song et al.

(10) Patent No.: US 11,511,255 B2
(45) Date of Patent: Nov. 29, 2022

(54) APPARATUS FOR PREPARING OLIGOMER

(71) Applicant: LG CHEM, LTD., Seoul (KR)

(72) Inventors: Jong Hun Song, Daejeon (KR); Jeong Seok Lee, Daejeon (KR); You Na Kim, Daejeon (KR); Hong Min Lee, Daejeon (KR); Moon Sub Hwang, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 17/267,407

(22) PCT Filed: May 20, 2020

(86) PCT No.: PCT/KR2020/006571
§ 371 (c)(1),
(2) Date: Feb. 9, 2021

(87) PCT Pub. No.: WO2021/075657
PCT Pub. Date: Apr. 22, 2021

(65) Prior Publication Data
US 2021/0362118 A1    Nov. 25, 2021

(30) Foreign Application Priority Data
Oct. 17, 2019    (KR) .................... 10-2019-0128837

(51) Int. Cl.
*B01J 4/00* (2006.01)
*B01J 19/24* (2006.01)
(Continued)

(52) U.S. Cl.
CPC ............ *B01J 19/002* (2013.01); *B01J 4/008* (2013.01); *B01J 12/00* (2013.01); *B01J 19/0053* (2013.01);
(Continued)

(58) Field of Classification Search
None
See application file for complete search history.

(56) References Cited

U.S. PATENT DOCUMENTS 8,058,369 B2 * 11/2011 Schneider ................ B01J 8/006
526/74
9,810,492 B2 * 11/2017 Tomkins ................... F28G 9/00
(Continued)

FOREIGN PATENT DOCUMENTS

EP        1777209 A1    4/2007
JP    2009-511721 A    3/2009
(Continued)

*Primary Examiner* — Jennifer A Leung
(74) *Attorney, Agent, or Firm* — Dentons US LLP

(57) ABSTRACT

Provided is an apparatus for preparing oligomer including: a reactor for carrying out oligomerization reaction by supplying a monomer stream and a solvent stream; and line 1 and line 2 which are separately provided in a lower side of the reactor, wherein line 1 includes a first level control valve and line 2 includes a second level control valve, and the reactor is periodically alternately operated in first operation mode and second operation mode, thereby switching a pipe through which the product is discharged, so that a plugging phenomenon of the pipe through which the product is discharged and the valve can be prevented.

7 Claims, 2 Drawing Sheets

(51) Int. Cl.
*C07C 2/08* (2006.01)
*B01J 19/00* (2006.01)
*B01J 12/00* (2006.01)

(52) U.S. Cl.
CPC .............. *B01J 19/24* (2013.01); *C07C 2/08* (2013.01); *B01J 2219/00164* (2013.01); *B01J 2219/00182* (2013.01); *B01J 2219/00247* (2013.01); *B01J 2219/00252* (2013.01); *B01J 2219/00389* (2013.01); *B01J 2219/2419* (2013.01)

(56) References Cited

U.S. PATENT DOCUMENTS

| | | | |
|---|---|---|---|
| 10,232,339 B2* | 3/2019 | Bischof | B01J 19/1843 |
| 10,370,307 B2* | 8/2019 | Boutrot | C07C 2/08 |
| 10,758,881 B2* | 9/2020 | Alqahtani | B01J 4/00 |
| 2012/0053304 A1 | 3/2012 | Fouarge et al. | |
| 2012/0080093 A1* | 4/2012 | Schneider | C08F 10/00 422/119 |
| 2013/0269730 A1* | 10/2013 | McGregor | B01J 19/18 134/166 R |
| 2017/0210680 A1* | 7/2017 | Azam | B01J 31/143 |
| 2017/0313798 A1 | 11/2017 | Hottovy et al. | |
| 2019/0083950 A1 | 3/2019 | Schwerdtfeger et al. | |
| 2019/0263733 A1 | 8/2019 | Fern et al. | |
| 2022/0041774 A1* | 2/2022 | Weitzel | C08F 2/22 |

FOREIGN PATENT DOCUMENTS

| | | |
|---|---|---|
| KR | 1998-702799 A | 8/1998 |
| KR | 2002-0050861 A | 6/2002 |
| KR | 2007-0004690 A | 1/2007 |
| KR | 10-1176388 B1 | 8/2012 |
| KR | 10-2013-0059401 A | 6/2013 |
| KR | 10-2018-0073501 A | 7/2018 |
| KR | 10-2019-0011245 A | 2/2019 |
| KR | 10-2019-0100964 A | 8/2019 |
| WO | 2011-112184 A1 | 9/2011 |
| WO | 2017-085097 A1 | 5/2017 |

* cited by examiner

[FIG. 1]
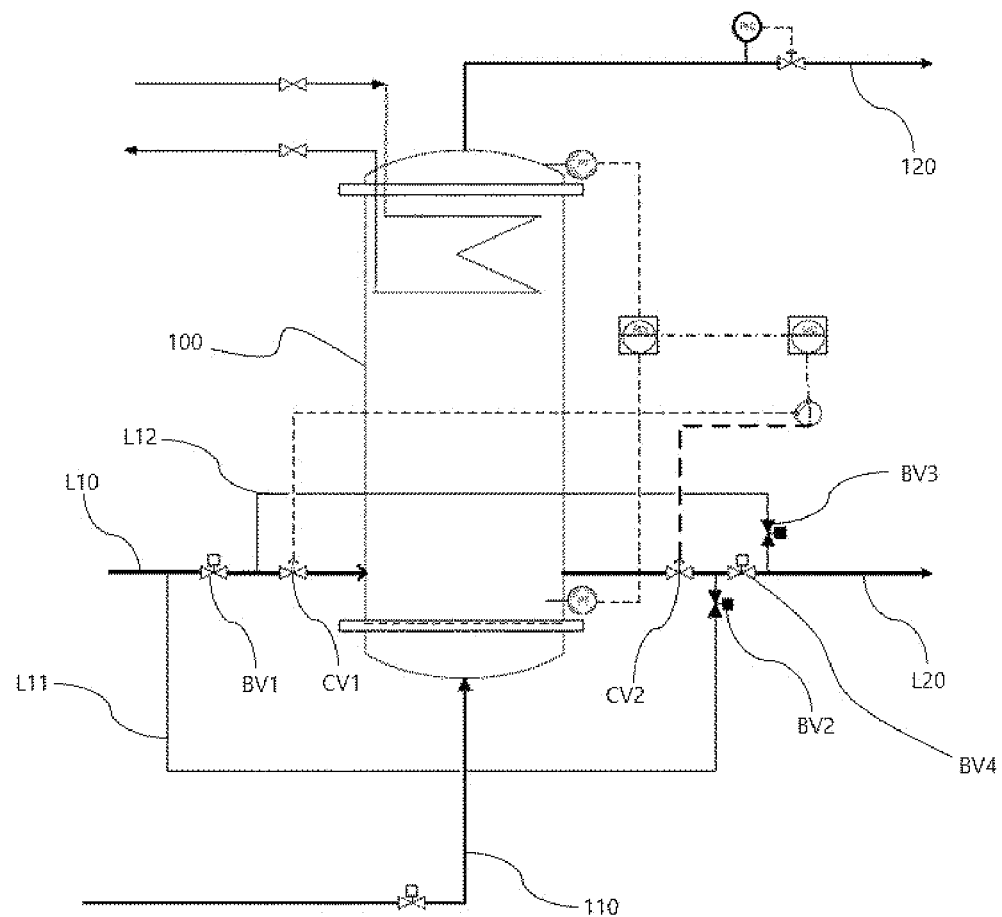

[FIG. 2]
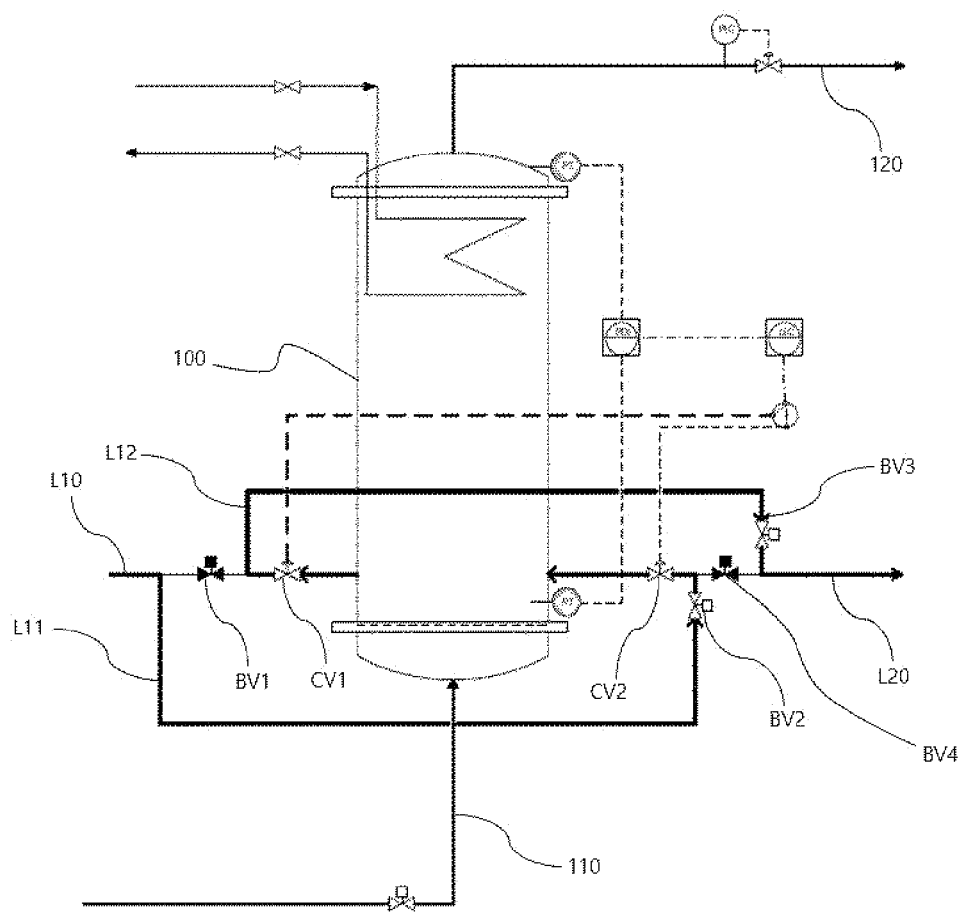

APPARATUS FOR PREPARING OLIGOMER

CROSS-REFERENCE TO RELATED APPLICATIONS

The present application is a National Phase entry pursuant to 35 U.S.C. § 371 of International Application No. PCT/KR2020/006571, filed on May 20, 2020, and claims the benefit of and priority to Korean Patent Application No. 10-2019-0128837, filed on Oct. 17, 2019, the entire contents of which are incorporated by reference in their entirety for all purposes as if fully set forth herein.

TECHNICAL FIELD

Technical Field

The present invention relates to an apparatus for preparing oligomer, and more particularly, to apparatus for preparing oligomer for preventing a plugging phenomenon occurring in pipes, valves, and the like in the production of an oligomer.

Background Art

An alpha-olefin is an important material which is used in copolymers, cleaning agents, lubricants, plasticizers, and the like and is commercially widely used, and in particular, 1-hexene and 1-octene are often used as a comonomer for adjusting the density of polyethylene in the production of linear low-density polyethylene (LLDPE).

The alpha-olefin such as 1-hexene and 1-octene is produced representatively by an oligomerization reaction of ethylene. The ethylene oligomerization reaction is carried out by an oligomerization reaction (trimerization reaction or tetramerization reaction) of ethylene in the presence of a catalyst using ethylene as a reactant, and the product produced by the reaction includes not only a multi-component hydrocarbon mixture including 1-hexene and 1-octene to be desired but also a small amount of wax and a polymer material during catalysis, thereby causing a plugging phenomenon in which the material is deposited on a reactor inner wall, and a pipe through which the product is discharged and a valve to block the pipe.

When plugging occurs in a product discharge pipe and a valve of the reactor, reactor operation should be shut down for cleaning the pipe and the valve, thereby causing a problem of a decrease in production due to an operation time reduction and also an increase in costs required in the cleaning process.

Thus, conventionally, a cleaning method for removing pollutants (wax, a polymer, and the like) deposited on a reactor and a pipe and a valve around the reactor and an effort to shorten a cleaning time have been continuously progressed. However, a study for extending an operation time of the reactor by fundamentally preventing the plugging phenomenon of the pipe and valve around the reactor is needed, rather than cleaning of the reactor.

DISCLOSURE

Technical Problem

In order to solve the problems mentioned in the above Background Art, an object of the present invention is to provide apparatus for preparing oligomer which is alternately operated in a first operation mode and a second operation mode, thereby switching a pipe through which a product is discharged, so that a plugging phenomenon in a pipe through which a product is discharged and a valve is prevented and an operation time of a reactor is extend to solve a problem of a decrease in production and to reduce costs required in a cleaning process.

Technical Solution

In one general aspect, an apparatus for preparing oligomer includes: a reactor for carrying out an oligomerization reaction by supplying a monomer stream and a solvent stream; and line 1 and line 2 which are separately provided in a lower side of the reactor, wherein line 1 includes a first level control valve and line 2 includes a second level control valve, and the reactor is periodically alternately operated in a first operation mode in which the solvent stream is supplied to the reactor through line 1 via the first level control valve and a stream including an oligomer product is discharged through line 2 via the second level control valve and in a second operation mode in which the solvent stream is supplied through line 2 connected to line 1-1 separated from line 1 via the second level control valve and the stream including an oligomer product is discharged through line 2 connected to line 1-2 separated from line 1 via the first level control valve of line 1.

Advantageous Effects

According to the apparatus for preparing oligomer of the present invention, the apparatus is alternately operated in the first operation mode and the second operation mode, thereby switching a pipe through which the product is discharged, so that a plugging phenomenon of the pipe through which the product is discharged and the valve can be prevented.

In addition, the present invention prevents the plugging phenomenon of the pipe through which the product is discharged and the valve, thereby solving a problem of a decrease in production occurring in a shutdown for cleaning and a cleaning cost increase problem.

DESCRIPTION OF DRAWINGS

FIG. 1 is a process flow diagram of apparatus for preparing oligomer which is operated in a first operation mode according to an exemplary embodiment of the present invention.

FIG. 2 is a process flow diagram of an apparatus for preparing oligomer which is operated in a second operation mode according to an exemplary embodiment of the present invention.

BEST MODE

The terms and words used in the description and claims of the present invention are not to be construed limitedly as having general or dictionary meanings but are to be construed as having meanings and concepts meeting the technical ideas of the present invention, based on a principle that the inventors are able to appropriately define the concepts of terms in order to describe their own inventions in the best mode.

In the present invention, the term, "stream" can refer to a fluid flow in a process, or can refer to a fluid itself flowing in a moving line (pipe). Specifically, the "stream" can refer to both a fluid itself flowing in a pipe connecting each apparatus and a fluid flow. In addition, the fluid can refer to a gas or a liquid.

Hereinafter, the present invention will be described in more detail referring to the following FIGS. 1 and 2, for better understanding of the present invention.

According to the present invention, an apparatus for preparing oligomer is provided. The apparatus for preparing oligomer includes: a reactor for carrying out an oligomerization reaction by supplying a monomer stream and a solvent stream; and line 1 and line 2 which are separately provided in a lower side of the reactor, wherein line 1 includes a first level control valve and line 2 includes a second level control valve, and the reactor is periodically alternately operated in a first operation mode in which the solvent stream is supplied to the reactor through line 1 via the first level control valve and a stream including an oligomer product is discharged through line 2 via the second level control valve and in a second operation mode in which the solvent stream is supplied through line 2 connected to line 1-1 separated from line 1 via the second level control valve and the stream including an oligomer product is discharged through line 2 connected to line 1-2 separated from line 1 via the first level control valve of line 1.

According to an exemplary embodiment of the present invention, a reactor 100 can be for producing an oligomer by oligomerizing a monomer in the presence of a catalyst and a solvent.

According to an exemplary embodiment of the present invention, the reactor 100 can be a reactor 100 appropriate for a continuous process. For example, the reactor 100 can include one or more reactors selected from the group consisting of a continuous stirred-tank reactor, a plug flow reactor, and a bubble column reactor. Thus, an oligomer product can be continuously produced.

According to an exemplary embodiment of the present invention, the monomer can include ethylene. Specifically, a monomer stream including an ethylene monomer is supplied to the reactor 100 to go through an oligomerization reaction to produce a desired alpha-olefin product. Here, the oligomerization reaction is carried out in a lower or a middle area of the reactor 100, and the oligomerization reaction of the monomer can be carried out in the state of a liquid dissolved in a solvent in the presence of a catalyst and a cocatalyst. The oligomerization reaction can refer to a reaction in which a monomer is oligomerized. The oligomerization can be referred to as trimerization or tetramerization depending on the number of monomers to be polymerized, and these are collectively called multimerization.

The alpha-olefin is an important material which is used in copolymers, cleaning agents, lubricants, plasticizers, and the like and is commercially widely used, and in particular, 1-hexene and 1-octene are often used as a comonomer for adjusting the density of polyethylene in the production of linear low-density polyethylene (LLDPE). The alpha-olefin such as 1-hexene and 1-octene can be produced by for example, a trimerization reaction or a tetramerization reaction of ethylene.

According to an exemplary embodiment of the present invention, the oligomerization reaction can be carried out by a homogeneous liquid phase reaction, a slurry reaction in the form in which a catalyst is partially not dissolved or entirely not dissolved, a two-phase liquid/liquid reaction, or a bulk phase reaction or gas phase reaction in which a product acts as a main medium, in the presence or absence of a solvent, by applying the reaction system and a common contact technology.

The catalyst can include a transition metal source. The transition metal source can be, for example, a compound including one or more selected from the group consisting of chromium (III) acetylacetonate, chromium (III) chloride tetrahydrofuran, chromium (III) 2-ethylhexanoate, chromium (III) tris(2,2,6,6-tetramethyl-3,5-heptanedionate), chromium (III) benzoylacetonate, chromium (III) hexafloro-2,4-pentanedionate, chromium (III) acetatehydroxide, chromium (III) acetate, chromium (III) butyrate, chromium (III) pentanoate, chromium (III) laurate, and chromium (III) stearate.

The cocatalyst can include one or more selected from the group consisting of trimethyl aluminum, triethyl aluminum, triisopropyl aluminum, triisobutyl aluminum, ethylaluminum sesquichloride, diethylaluminum chloride, ethyl aluminum dichloride, methylaluminoxane, modified methylaluminoxane, and borate.

As such, in the process of oligomerizing a monomer in the presence or absence of the catalyst and the solvent, by-products such as wax and a polymer are produced in addition to the oligomer product. When the by-product is discharged together with the oligomer product through the pipe, the by-product is deposited on a pipe inner wall and inside the valve due to stickiness of the polymer, to block the pipe and the valve.

In this regard, in the present invention, the apparatus 100 is alternately operated in the first operation mode and the second operation mode, thereby switching a pipe through which the product is discharged, so that a plugging phenomenon of the pipe through which the product is discharged and the valve can be prevented.

Specifically, when the product including by-products is continuously discharged through one pipe, deposition of the by-products is accumulated to block the pipe and the valve. However, in the present invention, the apparatus is operated in the first operation mode and the second operation mode to alternately switch a pipe to which the solvent stream is supplied and a pipe through which the oligomer product is discharged, and thus, even in the case in which accumulation due to by-products partially occurs in the pipe through which the oligomer product is discharged in the previous operation mode, an operation mode is changed to supply the solvent in a reverse direction to the pipe through which the oligomer products were previously discharged and the valve, so that the by-products which are partially accumulated in the pipe and the valve can be dissolved with the solvent or released to be removed. Thus, blockage of the pipe and the valve around the reactor 100 by the by-products can be prevented and a frequency of shutdown and cleaning can be significantly decreased to solve a problem of a decrease in production and to reduce cleaning costs.

According to an exemplary embodiment of the present invention, the monomer stream and the solvent stream can be supplied to the reactor 100 to carry out an oligomerization reaction.

The monomer stream can be supplied to the reactor 100 through a monomer stream supply line 110 provided in a lower portion of the reactor 100. Here, the monomer can be supplied in a gaseous state to the reactor 100. Specifically, the monomer stream including a gaseous monomer can be supplied to the reactor 100 through the monomer stream supply line 110 provided in the lower portion of the reactor 100, and the gaseous monomer can be dissolved in a solvent supplied to the reactor 100 to carry out the oligomerization reaction in a liquid phase.

The monomer stream can be supplied from a naphtha cracking center (NCC). The naphtha cracking process can be carried out by including a step of introducing each of naphtha, C2 and C3 hydrocarbon compounds, propane, and the like to a supply raw material and carrying out cracking in each pyrolysis furnace; a step of cooling cracking gas which was pyrolyzed in each pyrolysis furnace to include hydrogen, and C1, C2, and C3 or higher hydrocarbon compounds; a step of compressing the cooled cracking gas; and a step of purifying a cracking compression stream including hydrogen, and C1, C2, and C3 or higher hydrocarbon compounds. Here, the monomer stream can be a stream including ethylene (C2) separated from naphtha cracking.

The solvent can include one or more selected from the group consisting of n-pentane, n-hexane, n-heptane, cyclohexane, methylcyclohexane, octane, cyclooctane, decane, dodecane, benzene, xylene, 1,3,5-trimethylbenzene, toluene, ethylbenzene, chlorobenzene, dichlorobenzene, and trichlorobenzene.

The solvent can be used in combination of two or more, if necessary. Thus, a gaseous ethylene monomer can be liquefied at a higher temperature and a dissolution rate at which the gaseous ethylene monomer is dissolved in the solvent can be improved.

According to an exemplary embodiment of the present invention, an unreacted monomer discharge line 120 for discharging a stream including an unreacted monomer which was not dissolved in the solvent and did not participate in the oligomerization reaction can be further included in an upper portion of the reactor 100. The stream including an unreacted monomer can be in a gaseous state. The unreacted monomer can be reused in the oligomerization reaction by separating and collecting the unreacted monomer from the stream including a gaseous unreacted monomer discharged from the unreacted monomer discharge line 120 and resupplying the unreacted monomer to the reactor 100.

The oligomerization reaction which is carried out by supplying the monomer stream and the solvent stream supplied to the reactor 100 can be carried out at a temperature of 10° C. to 180° C., 30° C. to 150° C., or 50° C. to 120° C. In addition, the oligomerization reaction can be carried out under a pressure of 10 bar to 70 bar. For example, the oligomerization reaction can be carried out under a pressure of 10 bar to 70 bar, 20 bar to 65 bar, or 30 bar to 60 bar. When ethylene is oligomerized within the temperature range and the pressure range, a selectivity to desired alpha-olefin can be excellent, a by-product amount can be decreased, the operational efficiency of a continuous process can be increased, and the costs can be reduced.

The liquid stream including an oligomer product by the oligomerization reaction can be discharged from the reactor 100 through line 1 L10 or line 2 L20 which are separately provided in a lower side of the reactor 100. Here, line 1 L10 and line 2 L20 can be formed at the same height.

Specifically, in the present invention, when the reactor 100 is operated in the first operation mode, the stream including an oligomer product can be discharged through line 2 L20 and the solvent can be supplied through line 1 L10, and when the reactor 100 is operated in the second operation mode, the stream including an oligomer product can be discharged through line 10 and the solvent can be supplied through the second line L20. As such, the reactor 100 is periodically alternately operated in the first operation mode and the second operation mode, thereby preventing a plugging phenomenon occurring in the pipe and the valve around the reactor 100.

According to an exemplary embodiment of the present invention, in order to maintain catalysis in the reactor 100 constant, a liquid level can be adjusted. For this, a first level control valve CV1 can be provided in line 1 L10 and a second level control valve CV2 can be provided in line 2 L20.

According to an exemplary embodiment of the present invention, when the reactor 100 is operated in the first operation mode, the first level control valve CV1 formed in an arbitrary area of line 1 L10 maintains a 100% open state so as not to be an obstacle to the solvent stream supplied to the reactor 100, and when the reactor 100 is operated in the second operation mode, a level of the reactor 100 can be adjusted by adjusting the flow rate of the stream including an oligomer product discharged from the reactor 100. Specifically, the first level control valve CV1 can be formed in an area adjacent to the reactor 100 in line 1 L10.

In addition, when the reactor 100 is operated in the first operation mode, the second level control valve CV2 formed in an arbitrary area of line 2 L20 adjusts the level of the reactor 100 by adjusting the flow rate of the stream including an oligomer product discharged from the reactor 100, and when the reactor 100 is operated in the second operation mode, the second level control valve CV2 can maintain a 100% open state so as not to be an obstacle to the solvent stream supplied to the reactor 100. Specifically, the second level control valve CV2 can be formed in an area adjacent to the reactor 100 in line 2 L20.

According to an exemplary embodiment of the present invention, when the reactor 100 is operated in the first operation mode, the stream passing through the first level control valve CV1 of line 1 L10 can flow in a direction toward the reactor 100 and the stream passing through the second level control valve CV2 of line 2 L20 can flow in an opposite direction to the reactor 100, and when the reactor 100 is operated in the second operation mode, the stream passing through the first level control valve CV1 of line 1 L10 can flow in the opposite direction to the reactor 100 and the stream passing through the second level control valve CV2 of line 2 L20 can flow in a direction toward the reactor 100.

Specifically, when the reactor 100 is operated in the first operation mode, the solvent passes through the first level control valve CV1 of line 1 L10 to be supplied to the reactor 100, and the stream including an oligomer product passes through the second level control valve CV2 of line 2 L20 to be discharged from the reactor 100. In addition, when the reactor 100 is operated in the second operation mode, the stream including an oligomer product passes through the first level control valve CV1 of line 1 L10 to be discharged from the reactor 100, and the solvent passes through the second level control valve CV2 of line 20 L20 to be supplied to the reactor 100.

As such, the reactor 100 is alternately operated in the first operation mode and the second operation mode to change lines discharging the stream including an oligomer product, and thus, even in the case in which by-products are accumulated in the line through which the stream including an oligomer product is discharged and the level control valve, the accumulated by-products can be dissolved by the solvent or released, thereby significantly decreasing a problem of shutdown for cleaning the pipe and the valve around the reactor 100.

According to an exemplary embodiment of the present invention, line 1 L10 includes line 1-1 L11 separated from line 1 L10, and line 1-1 can be extended from line 1 L10 to be connected to line 2 L20.

According to an exemplary embodiment of the present invention, when the reactor 100 is operated in the second operation mode, line 1-1 L11 is a line for connecting the solvent from line 1 L10 to line 2 L20 to supply the solvent. Specifically, line 1-1 L11 can be formed in a front end of an area where the first level control valve CV1 is formed, that is, a farther area than the area where the first level control valve CV1 of line 1 L10 is formed from the reactor 100, for example, an area adjacent to the solvent inlet.

As such, line 1-1 L11 is connected from the front end of the area where the first level control valve CV1 of line 1 L10 is formed to a rear end of the second level control valve CV2 of line 2 L20, and the solvent supplied to line 1-1 L11 passes through the second level control valve CV2 of line 2 L20 to be supplied to the reactor 100.

According to an exemplary embodiment of the present invention, line 1 L10 includes line 1-2 L12 separated from line 1 L10, and line 1-2 L12 can be extended from line 1 L10 to be connected to line 2 L20.

When the reactor 100 is operated in the second operation mode, line 1-2 L12 can be a line for connecting the stream including an oligomer product discharged through line 1 L10 to line 2 L20 to discharge the stream.

Specifically, line 1-2 L12 can be for connecting the stream including an oligomer product which passes through the first level control valve CV1 of line 1 L10 to be discharged from the reactor 100 to the rear end of an area where the second level control valve CV2 of line 2 L20 is formed, so that the stream is discharged through line 2 L20.

line 1-2 L12 is extended from an area between an area where line 1-1 L11 is formed and an area where the first level control valve CV1 is formed to be connected to the rear end of an area where the second level control valve CV2 of line 2 L20 is formed. Accordingly, the stream including an oligomer product which passes the first level control valve CV1 of line 1 L10 to be discharged is connected to line 2 L20 through line 1-2 L12 to be discharged through line 2 L20.

According to an exemplary embodiment of the present invention, line 1 L10, line 1-1 L11, line 1-2 L12, and line 2 L20 can further include a block valve for controlling the stream, when the reactor is operated in the first operation mode or the second operation mode.

According to an exemplary embodiment of the present invention, line 1 L10 can include a first block valve BV1 provided in a front end of the first level control valve CV1. Specifically, the first block valve BV1 can be provided in an area between an area where line 1-1 L11 is separated from line 1 L10 and an area where line 1-2 L12 is separated from Line 1 L10.

When the reactor 100 is operated in the first operation mode, the first block valve BV1 can be maintained in an open state, and when the reactor 100 is operated in the second operation mode, the first block valve BV1 can be maintained in a closed state.

According to an exemplary embodiment of the present invention, line 1-1 L11 can include a second block valve BV2 provided in a front end of a point connected to line 2 L20. Specifically, the second block valve BV2 can be formed in line 1-1 L11 separated from line 1 L10, and can be formed in an arbitrary area of a front end of a point where line 1-1 L11 and line 2 L20 are connected.

When the reactor 100 is operated in the first operation mode, the second block valve BV2 is maintained in a closed state, and when the reactor 100 is operated in the second operation mode, BV2 can be maintained in an open state.

According to an exemplary embodiment of the present invention, line 1-2 L12 can include a third block valve BV3 provided in a front end of the point connected to line 2 L20. Specifically, the third block valve BV3 can be formed in line 1-2 L12 separated from line 1 L10, and can be formed in an arbitrary area of a front end of a point where line 1-2 L12 and line 2 L20 are connected.

When the reactor 100 is operated in the first operation mode, the third block valve BV3 is maintained in a closed state, and when the reactor 100 is operated in the second operation mode, BV3 can be maintained in an open state.

According to an exemplary embodiment of the present invention, line 2 L20 can include a fourth block valve BV4 provided between a point connected to line 1-1 L11 and a point connected to line 1-2 L12. Specifically, the fourth block valve BV4 can be formed in an area between a point where line 1-1 L11 separated from line 1 L10 is connected to the second line L20 and a point where line 1-2 L12 separated from line 1 L10 is connected to line 2 L20.

When the reactor 100 is operated in the first operation mode, the fourth block valve BV4 is maintained in an open state, and when the reactor 100 is operated in the second operation mode, BV4 can be maintained in a closed state.

According to an exemplary embodiment of the present invention, when the reactor 100 is operated in the first operation mode, the first block valve BV1 and the fourth block valve BV4 can be opened, and the second block valve BV2 and the third block valve BV3 can be closed.

Specifically, when the reactor 100 is operated in the first operation mode, the solvent stream can be supplied to line 1 L10 and pass through the opened first block valve BV1 and the first level control valve CV1 to be supplied to the reactor 100, and the stream including an oligomer product can be discharged through line 2 L20 and pass through the opened second level control valve CV2 and the fourth block valve BV4 to be discharged from the reactor 100.

According to an exemplary embodiment of the present invention, when the reactor 100 is operated in the second operation mode, the second block valve BV2 and the third block valve BV3 can be opened, and the first block valve BV1 and the fourth block valve BV4 can be closed.

Specifically, when the reactor 100 is operated in the second operation mode, the solvent stream can be supplied to line 1 L10, be transferred to line 1-1 L11 of a front end of the closed first block valve BV1, pass through the opened second block valve BV2 to be transferred to line 2 L20, be transferred in an opposite direction to the closed fourth block valve BV4 in line 2 L20, and pass through the second level control valve CV2 to be supplied to the reactor 100. In addition, the stream including an oligomer product can be discharged through line 1 L10, pass through the opened first level control valve CV1 to be transferred through line 1-2 L12 between the closed first block valve BV1 and the first level control valve CV1, pass through the opened third block valve BV3 to be transferred to line 2 L20, and be discharged in the opposite direction to the fourth block valve BV4.

As such, as the reactor 100 is operated in the first operation mode or the second operation mode, the first block valve BV1 to the fourth block valve BV4 are opened or closed, and thus, the direction can be adjusted while a reverse flow of the stream is prevented.

According to an exemplary embodiment of the present invention, a control unit (not shown) for operating the reactor 100 in the first operation mode or the second operation mode can be further included. The control unit (not shown) can serve to open or close each of the first level control valve CV1, the second level control valve CV2, the first block valve BV1, the second block valve BV2, the third block valve BV4, and the fourth block valve BV4.

Specifically, the control unit (not shown) can control the first level control valve CV1 and the second level control valve CV2 in order to maintain the level of a liquid phase inside the reactor 100 at a constant level. In addition, when the reactor 100 is operated in the first operation mode, the control unit (not shown) can open the first block valve BV1 and the fourth block valve BV4 and close the second block valve BV2 and the third block valve BV3, and when the reactor 100 is operated in the second operation mode, the control unit can close the first block valve BV1 and the fourth block valve BV4 and open the second block valve BV2 and the third block valve BV3. Here, a system constituting the control unit (not shown) is not particularly limited as long as it can play the role.

According to an exemplary embodiment of the present invention, a cooling tube (not shown) for controlling an oligomerization reaction temperature inside the reactor 100 can be further included. Cooling water can be supplied to the cooling tube (not shown). Thus, some heat occurring in the reaction can be removed so that the oligomerization reaction of the reactant performed in the reactor 100 can be carried out at a constant temperature, and amounts of liquid low-boiling point olefin and solvent which are entrained with an unreacted monomer and discharged together with the stream including the unreacted monomer can be decreased.

According to an exemplary embodiment of the present invention, the first operation mode and the second operation mode can have a cycle of 0.1 hours to 12 hours and can be alternately operated. For example, the first operation mode and the second operation mode can have a cycle of 0.1 hours to 12 hours, 0.5 hours to 6 hours, or 1 hour to 4 hours, and can be alternately operated. Thus, blockage of the pipe and the valve by by-products having stickiness included in the stream including an oligomer product discharged from the reactor 100 can be prevented.

Specifically, when the reactor 100 is operated in the first operation mode, the by-products can be accumulated in line 2 L20 and the second level control valve CV2, and usually in the operation for 12 to 72 hours, the operation should be shut down and cleaned due to the accumulation of the by-products. However, in the present invention, operation is changed from the first operation mode to the second operation mode before 12 hours have passed, thereby changing a discharge line of the stream including an oligomer product and some accumulated by-products in line 2 L20 and the second level control valve CV2 are dissolved using the supplied solvent, thereby preventing the problem of blocking the second level control valve CV2 so that the level of the liquid phase inside the reactor 100 is not adjusted. In addition, the reactor 100 is periodically alternately operated in the first operation mode and the second operation mode, thereby removing the by-products accumulated in the pipe and the valve as described above, so that the cycle to shut down and clean the reactor 100 can be significantly increased. Thus, production is increased and cleaning costs are reduced.

According to an exemplary embodiment of the present invention, in the apparatus for preparing oligomer, devices required for oligomer production such as a valve (not shown), a condenser (not shown), a reboiler (not shown), a pump (not shown), a separation apparatus (not shown), a compressor (not shown), and a mixer (not shown) can be further installed.

Hereinabove, the apparatus for preparing oligomer according to the present invention has been described and illustrated in the drawings, but the description and the illustration in the drawings are the description and the illustration of only core constitutions for understanding of the present invention, and in addition to the process and apparatus described above and illustrated in the drawings, the process and the apparatus which are not described and illustrated separately can be appropriately applied and used for carrying out the apparatus for preparing oligomer according to the present invention.

The invention claimed is:

1. An apparatus for preparing oligomer comprising:
   a reactor for carrying out an oligomerization reaction by supplying a monomer stream and a solvent stream; and
   a first line and a second line which are separately provided in a lower side of the reactor,
   wherein the first line includes a first level control valve and the second line includes a second level control valve, and
   wherein the reactor is periodically alternately operated in a first operation mode in which the solvent stream is supplied to the reactor through the first line via the first level control valve and a stream including an oligomer product from the first operation mode is discharged through the second line via the second level control valve and in a second operation mode in which the solvent stream is supplied through the second line connected to a third line, which is branched from the first line, via the second level control valve and a stream including an oligomer product from the second operation mode is discharged through the second line connected to a fourth line, which is branched from the first line via the first level control valve of the first line.

2. The apparatus for preparing oligomer of claim 1, wherein the monomer stream is supplied to the reactor through a monomer stream supply line provided in a lower portion of the reactor.

3. The apparatus for preparing oligomer of claim 1, further comprising: an unreacted monomer discharge line for discharging a stream including an unreacted monomer from the reactor, in an upper portion of the reactor.

4. The apparatus for preparing oligomer of claim 1, wherein,
   when the reactor is operated in the first operation mode, the solvent stream passing through the first level control valve flows in a direction toward the reactor, and the stream including the oligomer product from the first operation mode passing through the second level control valve flows in a direction opposite to the reactor, and
   when the reactor is operated in the second operation mode, the stream including the oligomer product from the second operation mode passing through the first level control valve flows in a direction opposite to the reactor, and the solvent stream passing through the second level control valve flows in a direction toward the reactor.

5. The apparatus for preparing oligomer of claim 1, wherein,
   the first line includes a first block valve provided in a front end of the first level control valve,
   the third line, branched from the first line, includes a second block valve provided in an end of the third line adjacent to a point in which the third line is connected to the second line, the fourth line, branched from the first line, includes a third block valve provided in an end of the fourth line adjacent to a point in which the fourth line is connected to the second line, and the second line includes a fourth block valve provided between the point connected to the third line and the point connected to the fourth line.

6. The apparatus for preparing oligomer of claim 5, wherein, when the reactor is operated in the first operation mode, the first block valve and the fourth block valve are opened and the second block valve and the third block valve are closed, and when the reactor is operated in the second operation mode, the second block valve and the third block valve are opened and the first block valve and the fourth block valve are closed.

7. The apparatus for preparing oligomer of claim 1, wherein the reactor is one or more reactors selected from the group consisting of a continuous stirred-tank reactor, a plug flow reactor, and a bubble column reactor.

\* \* \* \* \*